(12) United States Patent
O'Brien et al.

(10) Patent No.: US 7,463,942 B2
(45) Date of Patent: *Dec. 9, 2008

(54) DENTAL PROSTHESIS MANUFACTURING PROCESS, DENTAL PROSTHESIS PATTERN & DENTAL PROSTHESIS MADE THEREBY

(75) Inventors: Michael J. O'Brien, Corvallis, OR (US); Derrick G. Luksch, Corvallis, OR (US)

(73) Assignee: GeoDigm Corporation, Chanhassen, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/113,810

(22) Filed: Apr. 25, 2005

(65) Prior Publication Data
US 2005/0251281 A1 Nov. 10, 2005

Related U.S. Application Data

(63) Continuation of application No. 09/656,255, filed on Sep. 6, 2000, now Pat. No. 6,915,178.

(51) Int. Cl.
*G06F 19/00* (2006.01)
(52) U.S. Cl. ............... 700/118; 700/97; 700/182
(58) Field of Classification Search ......... 700/119–120, 700/182, 98, 169, 195, 180; 264/17, 54, 264/101, 19, 16, 401; 425/389; 164/34, 164/41, 516, 35, 122.1; 433/20.1, 219, 221, 433/222, 208; 219/228
See application file for complete search history.

(56) References Cited

U.S. PATENT DOCUMENTS

| | | | |
|---|---|---|---|
| 2,194,790 A | 3/1940 | Glück | |
| 3,807,862 A | 4/1974 | Hatzenbuhler | |
| 4,081,019 A | 3/1978 | Kulig | |
| 4,273,580 A | 6/1981 | Shoher et al. | |
| 4,411,626 A | 10/1983 | Becker et al. | |
| 4,611,288 A | 9/1986 | Duret et al. | |

(Continued)

FOREIGN PATENT DOCUMENTS

DE 36 26 789 A1 2/1988

(Continued)

OTHER PUBLICATIONS

Frank Hermanek, Finding The Lost Wax ProcessJan.-Feb. 2002, pp. 5 & 7.*

(Continued)

*Primary Examiner*—Kidest Bahta
(74) *Attorney, Agent, or Firm*—Merchant & Gould P.C.

(57) ABSTRACT

A dental prosthesis is made by first forming a model of a patient's dentition. A three dimensional digital data corresponding to the surfaces of the model is then created. Based on this data, a three dimensional digital data file is then created substantially corresponding to the dental prosthesis to be manufactured. The three dimensional digital data of the dental prosthesis to be manufactured is next transmitted to automated prototyping equipment, and using the automated prototyping equipment, a wax pattern of the dental prosthesis is manufactured based upon this three dimensional digital data of the dental prosthesis. Finally, using this wax pattern in the lost wax investment casting process, the dental prosthesis is made. Prior to investment casting, marginal edges of the wax pattern are adjusted manually.

12 Claims, 3 Drawing Sheets

U.S. PATENT DOCUMENTS

| | | | |
|---|---|---|---|
| 4,663,720 | A | 5/1987 | Duret et al. |
| 4,742,464 | A * | 5/1988 | Duret et al. .................. 700/183 |
| 4,844,144 | A | 7/1989 | Murphy et al. |
| 4,850,873 | A | 7/1989 | Lazzara et al. |
| 4,869,666 | A | 9/1989 | Talass |
| 4,952,149 | A | 8/1990 | Duret et al. |
| 4,972,897 | A | 11/1990 | Thomas |
| 5,011,405 | A | 4/1991 | Lemchen |
| 5,027,281 | A * | 6/1991 | Rekow et al. ................ 700/182 |
| 5,092,022 | A | 3/1992 | Duret |
| 5,139,419 | A | 8/1992 | Andreiko et al. |
| 5,232,361 | A | 8/1993 | Sachdeva et al. |
| 5,237,998 | A | 8/1993 | Duret et al. |
| 5,257,203 | A * | 10/1993 | Riley et al. .................. 700/163 |
| 5,338,198 | A | 8/1994 | Wu et al. |
| 5,368,478 | A | 11/1994 | Andreiko et al. |
| 5,431,562 | A | 7/1995 | Andreiko et al. |
| 5,447,432 | A | 9/1995 | Andreiko et al. |
| 5,454,717 | A | 10/1995 | Andreiko et al. |
| RE35,169 | E | 3/1996 | Lemchen et al. |
| 5,518,397 | A | 5/1996 | Andreiko et al. |
| 5,588,832 | A | 12/1996 | Farzin-Nia |
| 5,683,243 | A | 11/1997 | Andreiko et al. |
| 5,690,490 | A | 11/1997 | Cannon et al. |
| 5,725,376 | A | 3/1998 | Poirier |
| 5,735,692 | A * | 4/1998 | Berger ........................ 433/213 |
| 5,909,765 | A | 6/1999 | McDowell |
| 6,015,289 | A | 1/2000 | Andreiko et al. |
| 6,042,374 | A | 3/2000 | Farzin-Nia et al. |
| 6,049,743 | A | 4/2000 | Baba |
| RE36,863 | E | 9/2000 | Snyder |
| 6,152,731 | A | 11/2000 | Jordan et al. |
| 6,174,168 | B1 | 1/2001 | Dehoff et al. |
| 6,177,034 | B1 | 1/2001 | Ferrone |
| 6,217,334 | B1 | 4/2001 | Hultgren |
| 6,227,850 | B1 | 5/2001 | Chishti et al. |
| 6,283,753 | B1 * | 9/2001 | Willoughby ................ 433/172 |
| 6,287,121 | B1 | 9/2001 | Guiot et al. |
| 6,287,490 | B2 * | 9/2001 | Rheinberger et al. .......... 264/17 |
| 6,322,728 | B1 | 11/2001 | Brodkin et al. |
| 6,354,836 | B1 | 3/2002 | Panzera et al. |
| 6,371,761 | B1 | 4/2002 | Cheang et al. |
| 6,398,554 | B1 | 6/2002 | Perot et al. |
| 6,409,504 | B1 | 6/2002 | Jones et al. |
| 6,460,594 | B1 | 10/2002 | Lam |
| 6,463,344 | B1 | 10/2002 | Pavloskaia et al. |
| 6,506,054 | B2 | 1/2003 | Shoher et al. |
| 6,532,299 | B1 | 3/2003 | Sachdeva et al. |
| 6,568,936 | B2 | 5/2003 | MacDougald et al. |
| 6,648,640 | B2 | 11/2003 | Rubbert et al. |
| 6,648,645 | B1 | 11/2003 | MacDougald et al. |
| 6,667,112 | B2 | 12/2003 | Prasad et al. |
| 6,691,764 | B2 | 2/2004 | Embert et al. |
| 6,835,066 | B2 | 12/2004 | Iiyama et al. |
| 6,915,178 | B2 | 7/2005 | O'Brien et al. |
| 7,228,191 | B2 | 6/2007 | Hofmeister et al. |
| 2002/0015934 | A1 | 2/2002 | Rubbert et al |
| 2002/0110786 | A1 | 8/2002 | Dillier |
| 2004/0137408 | A1 | 7/2004 | Embert et al. |
| 2004/0204787 | A1 | 10/2004 | Kopelman et al. |
| 2004/0220691 | A1 | 11/2004 | Hofmeister |
| 2004/0265770 | A1 * | 12/2004 | Chapoulaud et al. .......... 433/24 |
| 2005/0177261 | A1 | 8/2005 | Durbin |
| 2005/0251281 | A1 | 11/2005 | O'Brien et al. |
| 2006/0106484 | A1 | 5/2006 | Saliger et al. |
| 2006/0115795 | A1 | 6/2006 | Marshall et al. |

FOREIGN PATENT DOCUMENTS

| | | | |
|---|---|---|---|
| EP | 0 316 106 A1 | | 5/1989 |
| EP | 0 322 257 A2 | | 6/1989 |
| EP | 0 426 363 A2 | | 5/1991 |
| EP | 0 502 227 B1 | | 11/1996 |
| EP | 0 781 625 A2 | | 7/1997 |
| EP | 1 006 931 | | 6/2000 |
| FR | 2 593 384 A1 | | 7/1987 |
| GB | 2 296 673 | | 7/1996 |
| JP | 5-49651 | | 3/1993 |
| SE | WO 95/15731 | * | 6/1995 |
| WO | WO 94/10935 | | 5/1994 |
| WO | WO 02/19940 A1 | | 3/2002 |
| WO | WO 02/076327 A1 | | 10/2002 |

OTHER PUBLICATIONS www.cranstoncasting.com/process.htm.*

Lewis, J., "Software beefs up tractor radiator-guard mount," *Design News*, vol. 54, No. 4, pp. 87-88 (Feb. 15, 1999)(1 page absract).

Rotert, V., "How one rapid prototyping method is able to eliminate tooling for investment casting," *Proceedings of the 45th Annual Technical Meeting and Exhibition Investment Casting Institute*, Atlanta, Georgia (1997) (1 page abstract).

Weeden, B. et al., "Alternative methods for custom implant production utilizing a combination of rapid prototyping technology and conventional investment casting," *Proceedings of the 1996 15th Southern Biomedical Engineering Conference*, Dayton Ohio (1996) (1 page abstract).

Wirtz, H. et al., "Investment casting shells in 1 day using selective laser sintering (SLS)," *Proceedings of the 24th BICTA Conference on Investment Casting*, Oxford, GB (1999) (1 page abstract).

Wu, M. et al., "Application of rapid prototyping and numerical simulation in titanium dental castings," *Computer Assisted Surgery & Rapid Prototyping in Medicine*, 5th Int. Workshop (1999) (1 page abstract).

* cited by examiner

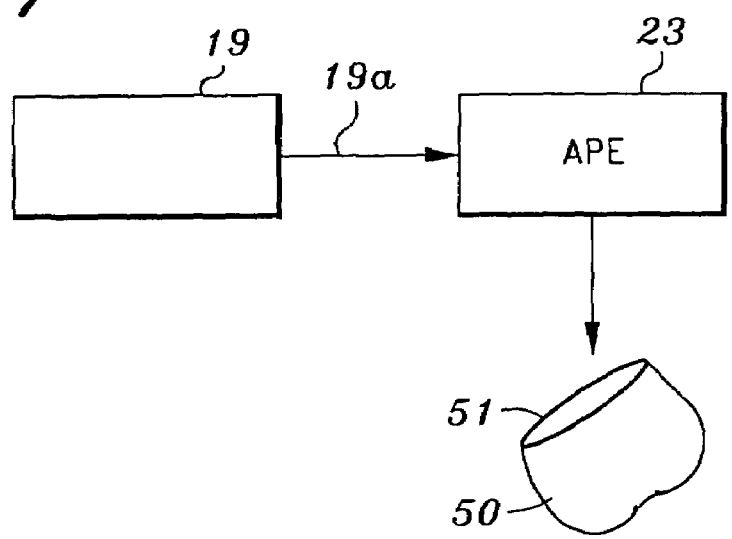
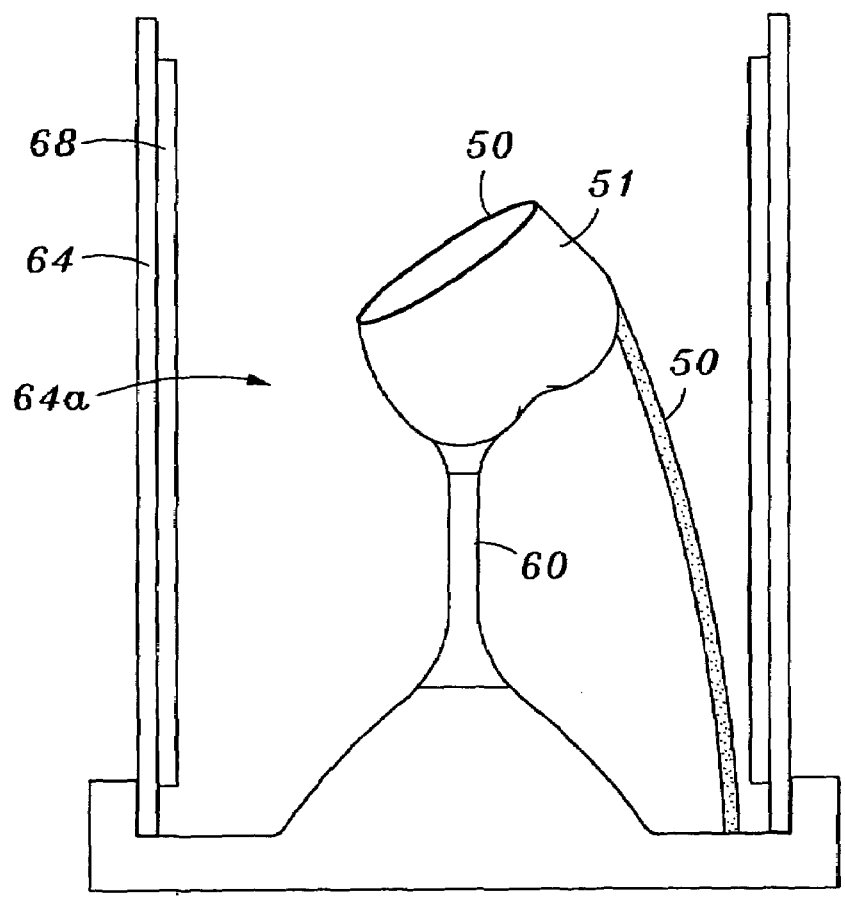

DENTAL PROSTHESIS MANUFACTURING PROCESS, DENTAL PROSTHESIS PATTERN & DENTAL PROSTHESIS MADE THEREBY

RELATED PATENT APPLICATION & INCORPORATION BY REFERENCE

This application is a continuation application of U.S. Ser. No. 09/656,255, entitled "DENTAL PROSTHESIS MANUFACTURING PROCESS, DENTAL PROSTHESIS PATTERN & DENTAL PROSTHESIS MADE THEREBY," filed Sep. 6, 2000, herein parent application, now U.S. Pat. No.6,915,178. This parent application is incorporated herein by reference and made a part of this application. Moreover, the inventors incorporate herein by reference any and all U.S. patents, U.S. patent applications, and other documents, hard copy or electronic, cited or referred to in this continuation, or the above-identified, parent application.

BACKGROUND OF THE INVENTION

Computer technology has advanced to the point where a dental prosthesis may be milled from a solid block of material based on three-dimensional digital data corresponding to a proposed shape of the dental prosthesis. The dentist first makes an impression of a patient's existing dentition. Typically, this includes nearby surfaces where the prosthesis is to be located in the patient's mouth. This is accomplished by the dentist first drilling away any unwanted dental tooth structure and then having the patient bite into an impression material that forms a negative impression of the patient's dentition, including the tooth structure to which the dental prosthesis is to be attached. This negative impression is then filled with dental die stone to make a model of the tooth structure to which the dental prosthesis is to be attached and adjacent teeth, particularly the teeth immediately above and to the sides of the tooth structure to which the dental prosthesis is to be attached. This model of the patient's dentition captures an impression of the occlusion surfaces between upper and lower aligned teeth and the configuration of the tooth structure to which the dental prosthesis is to be attached.

The computer aided design equipment used to make a dental prosthesis has an scanner that is used to scan the surfaces of the model. Scanning may be accomplished either with optical techniques using laser or non-laser light or tactile techniques where a probe physically contacts the tooth's surface. The computer aided design equipment converts the model's surfaces into three-dimensional digital data corresponding to the physical shape of the model. This original data collected during scanning is then used to create an image of the proposed shape for the prosthesis on a screen of a computer monitor. The computer aided design equipment is programmed to allow the user, with the aid of a mouse and employing conventional point and click techniques, to change the shape of the image. The original image displayed on the monitor screen needs to be adjusted to modify the original image to correspond to the ultimate shape of the dental prosthesis.

Because the data originally collected during scanning isn't precise enough to make the dental prosthesis directly based on this data, the user can and does make adjustments to the data originally provided by the scanner so that the dental prosthesis, at least in theory, fits properly into the patient's mouth. After making such adjustments to the data collected by the scanner, the adjusted three-dimensional digital data is then forwarded to an automatic milling machine which then mills away the unwanted material from a block to form the dental prosthesis. Typically, the block of material is a ceramic, titanium, or composite plastic material. One of the perceived advantages of this technique is the elimination of conventional investment casting of a wax pattern of the dental prosthesis, which has conventionally been used to make a dental prosthesis.

Although this computer aided design equipment proposes to eliminate conventional investment casting, it suffers from a number of drawbacks that prevent greater utilization of this technology. First, it is impractical to make dental prosthesis from such precious metals as gold and platinum using this technology because so much of the precious metal is lost during the milling process. Second, the adjustments made to the image based on the original data collected during scanning usually fail to create a dental prosthesis that properly fits into the patient's mouth. The inaccuracies in the shape of the dental prosthesis so produced using this technology are particularly acute along the marginal edges of the prosthesis adjacent the margins where the treated (drilled) tooth surfaces of an individual tooth are contiguous with the untreated (undrilled) tooth surfaces of this individual tooth.

SUMMARY OF THE INVENTION

This invention overcomes the drawbacks associated with the computer aided design technology that eliminates investment casting of a dental prosthesis and directly mills the prosthesis from a block of material. It has several features, no single one of which is solely responsible for its desirable attributes. Without limiting the scope of this invention as expressed by the claims that follow, its more prominent features will now be discussed briefly. After considering this discussion, and particularly after reading the section entitled, "DETAILED DESCRIPTION OF THE PREFERRED EMBODIMENT," one will understand how the features of this invention provide its benefits, which include, but are not limited to, (1) usage of precious metal in making a dental prosthesis with minimum waste of such metal, (2) improved accuracy of the marginal edges of the dental prosthesis positioned along the margins of a tooth structure, and (3) reduction of time to make a dental prosthesis using conventional investment casting techniques.

The invention includes a method of manufacturing a pattern of a dental prosthesis from a wax material, a method of manufacturing a dental prosthesis itself using this pattern, the dental prosthesis itself, and the pattern used in the manufacture of the dental prosthesis. As used herein, a dental prosthesis includes wax-ups (a term used in the industry) of articulated jaws. These wax-ups constitute an entire array of the teeth in an individual patient and they are used for diagnostic purposes. As used herein, "wax material" includes waxes, thermoplastics, combinations of wax and thermoplastic, or other ablative materials that are commonly used in the lost wax process.

The first step of the method of this invention is to form a model of a patient's dentition. This model includes surfaces corresponding to the dental structure nearby the location that the dental prosthesis is to be placed in the mouth of a patient.

The second step is to create three dimensional digital data corresponding to these surfaces, and based at least in part on this data, to create three dimensional digital data substantially corresponding to the dental prosthesis to be manufactured. Typically this is accomplished using a scanner to scan the surfaces of the model to collect three dimensional digital data corresponding to these surfaces. A monitor screen of computer aided design equipment displays an image of a proposed dental prosthesis based, at least in part, on the collected three dimensional digital data corresponding to the surfaces of the model. With the aid of the computer aided design equipment, the image is modified so that the modified image displayed on the monitor screen substantially corresponds to the dental prosthesis to be manufactured.

The third step is to transmit the three dimensional digital data of the dental prosthesis to be manufactured to automated prototyping equipment. Using the automated prototyping equipment, a wax pattern of the dental prosthesis is made from a wax material. This pattern is then used in the lost wax investment casting process to manufacture the dental prosthesis.

In accordance with this invention, the pattern has marginal edges that are at least ¾ of a millimeter from margins of an individual tooth structure to which the dental prosthesis is to be attached. These set back marginal edges of the pattern are manually adjusted to compensate for the specific configuration of the individual tooth structure by adding wax material to these set back marginal edges. This insures that the inaccuracies ordinarily occurring using computer aided design and milling equipment are avoided.

DESCRIPTION OF THE DRAWING

The preferred embodiment of this invention, illustrating all its features, will now be discussed in detail. This embodiment depicts the novel and non-obvious method of manufacturing a pattern of a dental prosthesis from a thermoplastic material, and pattern and dental prosthesis made by this method, as shown in the accompanying drawing, which is for illustrative purposes only. This drawing includes the following figures (Figs.), with like numerals indicating like parts:

FIG. 7 is a schematic diagram of computer aided design equipment connected to automated prototyping equipment that makes a pattern (referred to herein as wax pattern) of the dental prosthesis from wax material.

FIG. 8 is a schematic cross-sectional view showing a wax pattern of a crown type dental prosthesis positioned in a casting ring used in investment casting.

DETAILED DESCRIPTION OF THE PREFERRED EMBODIMENT

Figure 1:
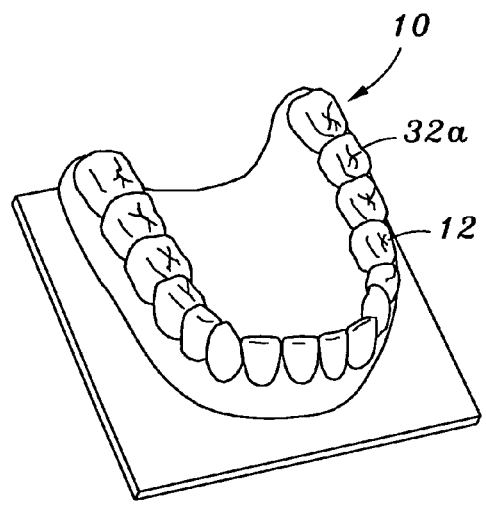
FIG. 1 is a perspective view of the upper jaw portion of a model for a patient's dentition.
Figure 1A:
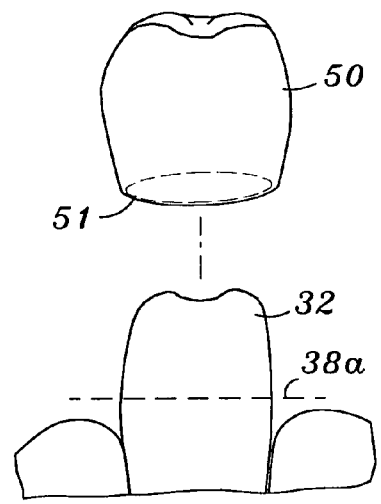
FIG. 1A is an enlarged fragmentary view of part of the upper jaw portion of the model for a patient's dentition shown in FIG. 1, depicting a stump on which a crown type dental prosthesis is to be attached.
Figure 2:
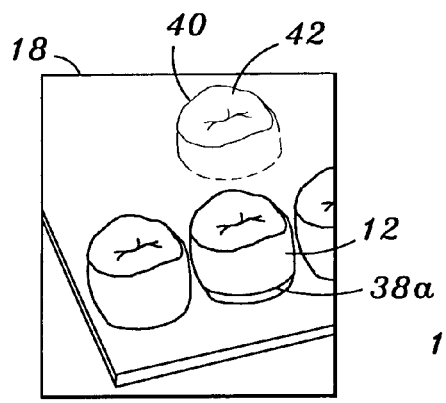
FIG. 2 is the monitor screen of computer aided design equipment programmed to create images of different shaped dental prosthesis.
Figure 6:
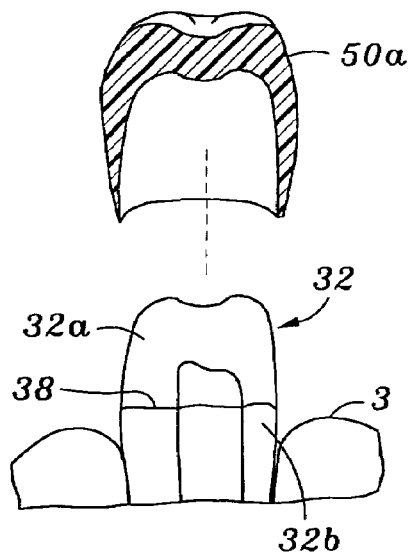
FIG. 6 is a side elevational view of a treated tooth structure to which a crown type dental prosthesis is to be attached.

In accordance with conventional techniques, a model of a patient's dentition is made. The upper jaw portion 10 of such a model is shown in FIG. 1. A lower jaw portion of this model is also used to collect tooth surface data, but is not shown. For purposes of illustration as shown in FIG. 6, an actual stump 32 to which a crown type 50a dental prosthesis is to be attached includes a drilled away portion 32a and an undisturbed portion 32b next to the patient's gum 34. Where the contiguous borders of the portions 32a and 32b meet, as defined by the line 38, a margin is formed. The jaw portion 10 includes a replicate 32a of the stump 32 to which the crown type dental prosthesis 50a is to be attached.

As shown in FIG. 6, computer aided design equipment 19 creates an image of a dental prosthesis based on data collected from the model of the patient's dentition. As illustrated in FIG. 7, computer aided design equipment sold under the trademark LabQraft™ by Dentalmatic Technologies, Inc. of St. Laurent, Quebec, Canada is modified in accordance with this invention to eliminate milling apparatus connected to an output 19a. In accordance with this invention, this output 19a is connected to automated prototyping equipment 23. Other similar type equipment such as sold by Decim AB of Skelleftea, Sweden, may also be modified by eliminating the milling equipment and used in accordance with this invention. Suitable automated prototyping equipment 23 is sold under the trademark ModelMaker II™ by Sanders Prototype, Inc. of Merrimack, N.H.

The equipment 19 includes an optical scanner 20 that scans the surfaces of the model of a patient's dentition by directing a beam of light from a source 17 at the model's surfaces, for example, at the tooth surfaces of the upper jaw portion 10. The reflected light represents information corresponding to the contours of these surfaces. This information is collected by a sensor 15 and then stored in the memory 22 of a computer 24 as three dimensional digital data. Various images of a dental prosthesis are displayed on a screen 18 of a monitor 30 connected to an output 32 of the computer 24 based on the data originally collected by the scanner 20. These images, and the corresponding data creating these images, are modified by the user using conventional input devices such as a mouse 26 and keyboard 28 to interact with, and modify, the originally collected three dimensional digital data.

Figure 3:
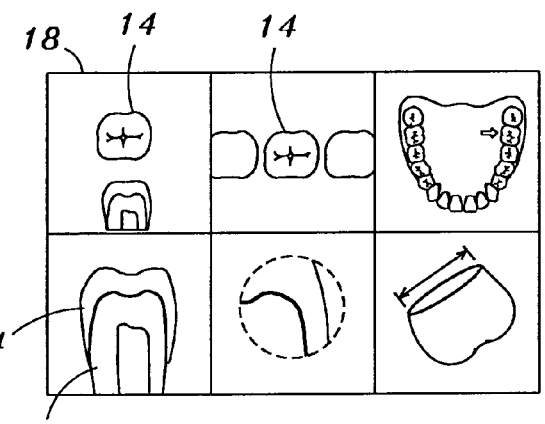
FIG. 3 is the monitor screen of computer aided design equipment displaying how different portions of an image of a dental prosthesis may be modified.
Figure 4:
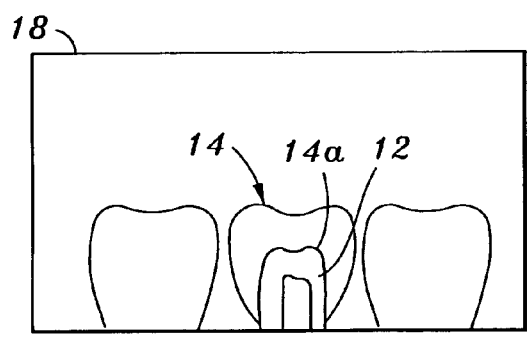
FIG. 4 is another view of the monitor screen showing a dental prosthesis mounted to a tooth structure.
Figure 5:
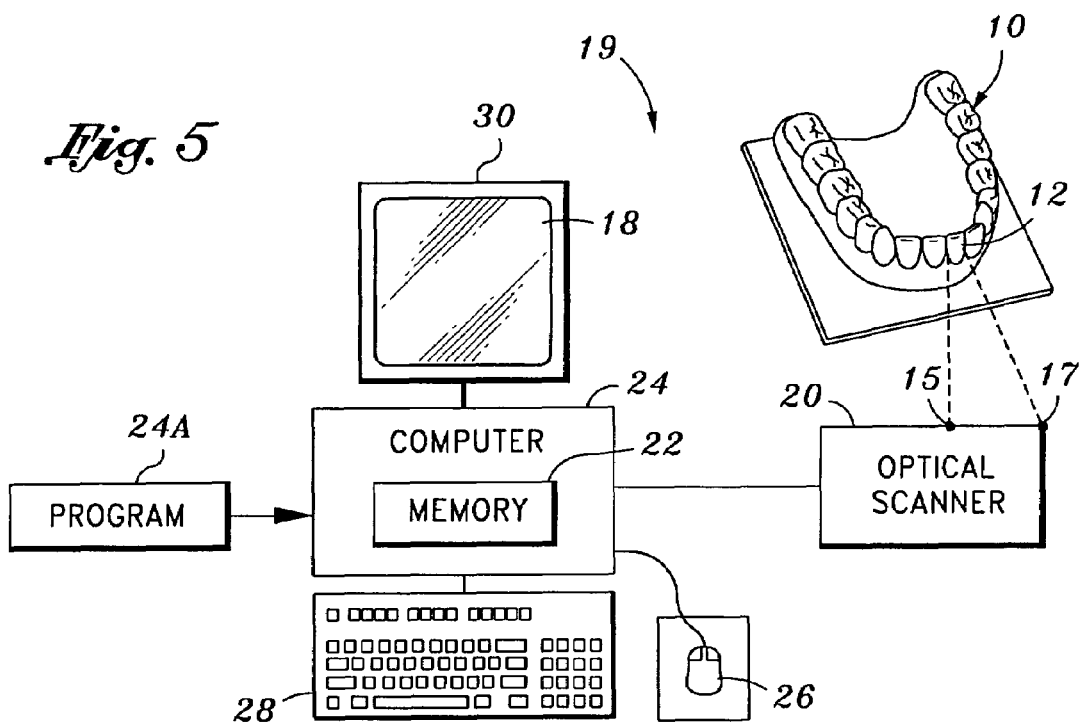
FIG. 5 is a schematic diagram of computer aided design equipment used in the method of this invention.

The numeral 12 is an image displayed on the screen 18 corresponding to the actual tooth structure, that is, the stump 32 (FIG. 6) that has been prepared by a dentist for a dental prosthesis. The image 12 is created upon optically scanning the surface of the replicate 32a of the stump 32 and manipulating the collected information of the surface contours, creating the image 12 in accordance with a program 24a that controls processing of the data by the computer 24. As depicted in FIGS. 3 and 4, an image 14 of the crown 50a to be attached to the stump 32 is displayed on the monitor's screen 18. In this example, an image 40 of the surface of an upper tooth immediately above and facing the stump 32 and an image 42 of the surface of the upper adjacent tooth are also displayed on the monitor's screen 18. Through the use of the mouse 26 and keyboard 28 the user can change parameters such as die spacer, minimum thickness of the prosthesis, contact points, grooves, cusp overlays and marginal ridges.

In accordance with this invention, the automated prototyping equipment 23 makes a wax pattern 50 (FIGS. 7 and 8) from wax material. This wax pattern 50 is based on the data collected during optical scanning. Typically, the pattern 50 is formed by a series of wax layers laid one upon another until the desired overall shape is completed. The wax pattern 50 formed by the method of this invention is at least ¾ millimeters from the margin line 38a corresponding to the actual margin line 38 as determined when the pattern 50 is seated by a dental technician on the replicate 32a of a stump 32. In other words, when the user is creating on the monitor screen 18 an image 14 of the crown 50a, the edges 14a of this image 14 are at least ¾ of a millimeter from an image 38a of the margin line displayed on the screen 18. Consequently, the wax pattern 50 has marginal edges 51 that are displaced at least ¾ millimeters from the margin line 38a on the replicate 32a that correspond to the actual margin line 38. In accordance with this invention, the edges 51 of the pattern 50 are then manually adjusted to compensate for the specific configuration of the stump 32 by adding a wax material to these edges. This avoids the inaccuracies associated with attempting to make a dental prosthesis that fits properly based solely on computer manipulation of data and then milling the prosthesis from a block of material as dictated by this data.

The wax pattern 50 produced by the automated prototyping equipment 23 is used in the conventional investment casting process to make the crown type dental prosthesis 50a. As shown in FIG. 8, the wax pattern 50 is attached to a sprue 60 made of wax material. This sprue 60 is mounted to a raised conical portion of a rubber base 62 and a metal ring 64 lined with a sheet 68 of ceramic fiber paper is seated on the base. Preferably, a wax rod 70 extends from a side portion of the pattern 50 to the base 62. The hollow interior 64a of the ring 64 and base 62 is then filled with the investment material, for example, a plaster, that is allowed to dry. After drying the assembly of the base 62, ring 64 and mounted wax pattern 50 is inverted and the base removed. The sprue 60 and wax pattern 50 are next removed by burning them away so that the casting is formed with a hollow cavity (not shown) into which molten metal is poured to form the crown 50a.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. For example, although only crowns have been illustrated, other dental prosthesis such as, for example, bridges and inlays can be made using this invention. Moreover, this method may also be used to make wax-ups of articulated jaws used for diagnostic purposes. Consequently, it is not the intention to limit this invention to the particular embodiment disclosed. On the contrary, the intention is to cover all modifications and alternate constructions coming within the spirit and scope of the invention as generally expressed by the following claims, which particularly point out and distinctly claim the subject matter of the invention:

The invention claimed is:

1. A method of manufacturing a pattern of a dental prosthesis, comprising:
   (a) collecting data substantially corresponding to an image of the dental prosthesis to be manufactured, the dental prosthesis having dimensions including a margin, and the image having a marginal edge substantially corresponding to the margin;
   (b) adjusting the collected data to set back the marginal edge of the image from the margin of the dental prosthesis to be manufactured;
   (c) transmitting said collected data to automated prototyping equipment; and
   (d) using the automated prototyping equipment, making the pattern of said dental prosthesis to be manufactured based upon said data, the pattern including the set back marginal edge.

2. The method of claim 1, further comprising:
   generating the image of the dental prosthesis to be manufactured.

3. The method of claim 2, wherein generating the image comprises:
   forming a model representing a dentition of a patient, the model having a surface;
   scanning the surface of the model to collect information regarding contours of the surface of the model; and
   processing the collected information to generate the image.

4. The method of claim 3, further comprising modifying the image of the dental prosthesis.

5. The method of claim 3, wherein scanning the surface of the model comprises:
   directing a beam of light at the surface with an optical scanner; and
   collecting reflected light at a sensor, the reflected light representing information corresponding to contours of the surface.

6. The method of claim 1, wherein making the pattern comprises making a wax pattern from a wax material.

7. The method of claim 1, further comprising:
   investing the pattern to form a casting;
   burning out the pattern from the casting to form a hollow cavity in the casting; and
   pouring molten metal into the hollow cavity of the casting to form the dental prosthesis.

8. A method of manufacturing a dental prosthesis, comprising:
   (a) collecting data substantially corresponding to an image of the dental prosthesis to be manufactured, the dental prosthesis having dimensions including a margin;
   (b) adjusting the collected data to set back the marginal edge of the image from the margin of the dental prosthesis to be manufactured;
   (c) transmitting said collected data to automated prototyping equipment;
   (d) using the automated prototyping equipment, making from a wax material a pattern of said dental prosthesis to be manufactured based upon said data, the pattern including the set back marginal edge; and
   (e) using said pattern in a lost wax investment casting process manufacturing said dental prosthesis.

9. A method of manufacturing a pattern of a dental prosthesis, comprising:
   (a) collecting data substantially corresponding to an image of the dental prosthesis to be manufactured, said image being modified to adjust marginal edges of the image to positions set back from margins of an individual tooth structure to which the dental prosthesis is to be attached, and transmitting said data to automated prototyping equipment; and
   (b) using the automated prototyping equipment, making the pattern of said dental prosthesis to be manufactured based upon said data,
   said pattern having marginal edges that are at least ¾ of a millimeter from the margins of the individual tooth structure to which the dental prosthesis is to be attached.

10. The method of claim 9 where the marginal edges of the pattern are manually adjusted to compensate for a specific configuration of said individual tooth structure.

11. The pattern of a dental prosthesis made by a method comprising:
   (a) collecting data substantially corresponding to an image of the dental prosthesis to be manufactured, the dental prosthesis having dimensions including a margin;

(b) adjusting the collected data to set back the marginal edge of the image from the margin of the dental prosthesis to be manufactured;
(c) transmitting said data to automated prototyping equipment; and
(d) using the automated prototyping equipment, making from a wax material the pattern of said dental prosthesis to be manufactured based upon said data, the pattern including the set back marginal edge.

12. The dental prosthesis made by a method comprising:
(a) collecting data substantially corresponding to an image of the dental prosthesis to be manufactured, the dental prosthesis having dimensions including a margin;
(b) adjusting the collected data to set back the marginal edge of the image from the margin of the dental prosthesis to be manufactured;
(c) transmitting said data to automated prototyping equipment;
(d) using the automated prototyping equipment, making from a wax material a pattern of said dental prosthesis to be manufactured based upon said data, the pattern including the set back marginal edge; and
(e) using said pattern in the lost wax investment casting process manufacturing said dental prosthesis.

* * * * *